United States Patent
Murakami et al.

(10) Patent No.: US 9,873,755 B2
(45) Date of Patent: Jan. 23, 2018

(54) METHOD OF MANUFACTURING WATER-ABSORBENT RESIN, WATER-ABSORBENT RESIN, WATER-ABSORBING AGENT AND ABSORBENT ARTICLE

(71) Applicant: Sumitomo Seika Chemicals Co. Ltd., Kako-gun, Hyogo (JP)

(72) Inventors: Masahiro Murakami, Himeji (JP); Tetsuhiro Hinayama, Himeji (JP); Hiroki Yabuguchi, Himeji (JP); Hideki Yokoyama, Himeji (JP)

(73) Assignee: Sumitomo Seika Chemicals Co. Ltd., Kako-gun (JP)

(*) Notice: Subject to any disclaimer, the term of this patent is extended or adjusted under 35 U.S.C. 154(b) by 0 days.

(21) Appl. No.: 14/787,716

(22) PCT Filed: Nov. 4, 2014

(86) PCT No.: PCT/JP2014/079246
§ 371 (c)(1),
(2) Date: Oct. 28, 2015

(87) PCT Pub. No.: WO2016/006133
PCT Pub. Date: Jan. 14, 2016

(65) Prior Publication Data
US 2017/0107313 A1    Apr. 20, 2017

(30) Foreign Application Priority Data

Jul. 11, 2014  (JP) .................................. 2014-143718
Oct. 31, 2014  (JP) .................................. 2014-223725

(51) Int. Cl.
| | | |
|---|---|---|
| C08F 120/06 | (2006.01) |
| A61F 13/49 | (2006.01) |
| A61F 13/53 | (2006.01) |
| A61L 15/24 | (2006.01) |
| A61L 15/60 | (2006.01) |
| C08F 2/18 | (2006.01) |
| C08F 2/32 | (2006.01) |
| C08J 3/24 | (2006.01) |
| C08K 3/22 | (2006.01) |
| C08K 3/34 | (2006.01) |
| C08K 3/36 | (2006.01) |

(52) U.S. Cl.
CPC ............ *C08F 120/06* (2013.01); *A61F 13/49* (2013.01); *A61F 13/53* (2013.01); *A61L 15/24* (2013.01); *A61L 15/60* (2013.01); *C08F 2/18* (2013.01); *C08F 2/32* (2013.01); *C08J 3/24* (2013.01); *C08K 3/22* (2013.01); *C08K 3/34* (2013.01); *C08K 3/36* (2013.01); *C08F 2810/20* (2013.01); *C08J 2333/02* (2013.01); *C08K 2003/2227* (2013.01)

(58) Field of Classification Search
CPC ............ C08F 120/06; C08J 3/24; C08K 3/22; C08K 3/34; C08K 3/36; A61F 13/49; A61F 13/53; A61L 15/24; A61L 15/60
USPC ........................................................ 524/430
See application file for complete search history.

(56) References Cited

U.S. PATENT DOCUMENTS

| | | |
|---|---|---|
| 5,180,798 A | 1/1993 | Nakamura et al. |
| 6,107,358 A | 8/2000 | Harada et al. |
| 2007/0179261 A1 | 8/2007 | Uda et al. |
| 2015/0216740 A1 | 8/2015 | Watanabe et al. |

FOREIGN PATENT DOCUMENTS

| | | | |
|---|---|---|---|
| CN | 1179433 A | 4/1998 | |
| CN | 1898270 A | 1/2007 | |
| EP | 0780424 A1 | 6/1997 | |
| EP | 0629411 B1 * | 10/2001 | ............. A61L 15/60 |
| JP | S61-271303 A | 12/1986 | |
| JP | S64-38406 A | 2/1989 | |
| JP | H03-227301 A | 10/1991 | |
| JP | H06-287233 A | 10/1994 | |
| JP | H06-345819 A | 12/1994 | |

(Continued)

OTHER PUBLICATIONS

JP2012-236898A—machine translation.*

(Continued)

*Primary Examiner* — Ling Choi
*Assistant Examiner* — Ronald Grinsted
(74) *Attorney, Agent, or Firm* — Locke Lord LLP

(57) ABSTRACT

With respect to water-absorbent resins, there are provided a method of manufacturing a water-absorbent resin having an appropriate BET specific surface and a water-absorption rate and a water-absorbing agent and an absorbent article that are formed by using the water-absorbent resin. In a first aspect of the present invention, when reverse phase suspension polymerization of two steps or more is performed on a water-soluble ethylenically unsaturated monomer in a hydrocarbon dispersion medium in the presence of at least an azo compound, a peroxide and an internal-crosslinking agent, the used amount of the internal-crosslinking agent at the time of the polymerization of a first step is adjusted to fall within a range of 0.015 to 0.150 mmol per mole of the water-soluble ethylenically unsaturated monomer used at the time of the polymerization of the first step and he polymerization is performed such that, the BET specific surface area of secondary particles formed by agglomeration of primary particles obtained is controlled.

10 Claims, 1 Drawing Sheet

(56) References Cited

FOREIGN PATENT DOCUMENTS

| JP | H08-120013 A | 5/1996 | |
|----|----|----|----|
| JP | H09-124710 A | 5/1997 | |
| JP | H11-335404 A | 12/1999 | |
| JP | 2012-236898 A | 12/2012 | |
| JP | 2012236898 A * | 12/2012 | ................ C08F 2/32 |
| WO | WO-2004/113452 A1 | 12/2004 | |
| WO | WO-2005/092956 A1 | 10/2005 | |
| WO | WO-2006/033477 A1 | 3/2006 | |
| WO | WO-2012/107432 A1 | 8/2012 | |
| WO | WO-2014038324 A1 | 3/2014 | |

OTHER PUBLICATIONS

International Search Report for PCT/JP2014/079246 dated Jul. 11, 2014.
Office Action dated Jan. 18, 2016, issued for Taiwanese Patent Application No. 104122057.
European Search Report dated Apr. 19, 2016, issued for EP Application No. 14882127.5.
Catalogue of Degussa, Aerosil & Silanes, Feb. 6, 2016, 132 pages.
Third Party Observation for European patent application No. 14882127 dated Jun. 7, 2016.

* cited by examiner

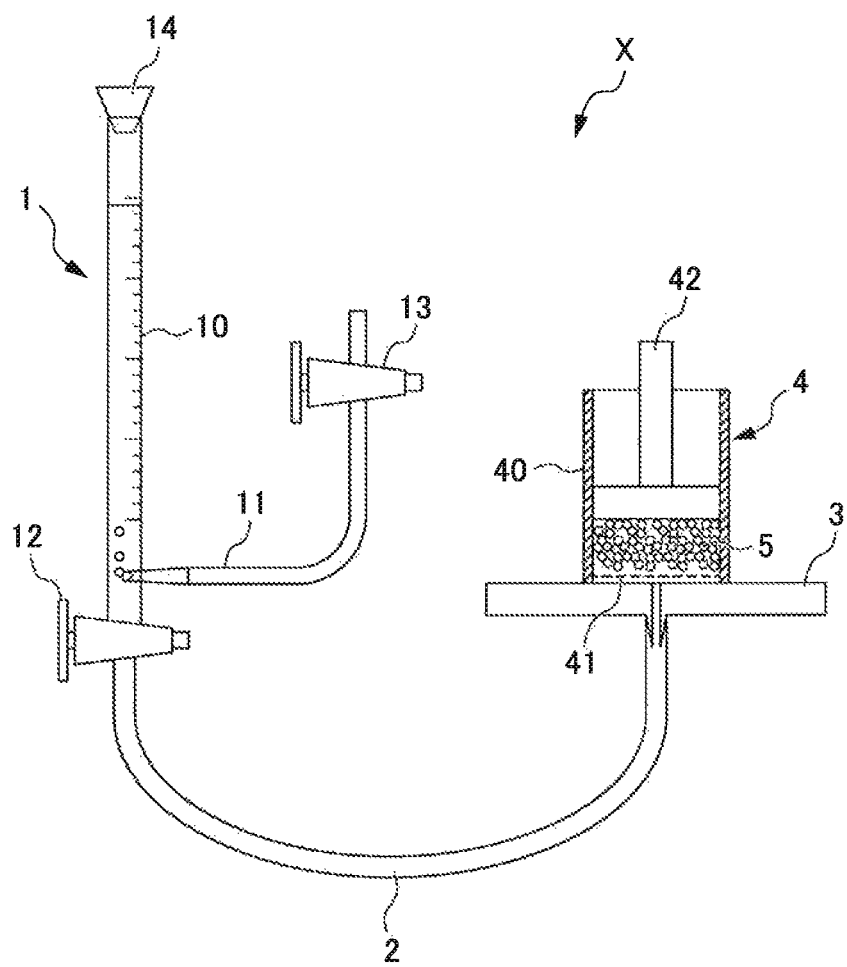

METHOD OF MANUFACTURING WATER-ABSORBENT RESIN, WATER-ABSORBENT RESIN, WATER-ABSORBING AGENT AND ABSORBENT ARTICLE

CROSS-REFERENCE TO RELATED APPLICATIONS

This application is the national phase under 35 U.S.C. §371 of PCT International Application No. PCT/JP2014/079246, filed Nov. 4, 2014, which claims the benefit of Japanese Application No. 2014-143718, filed Jul. 11, 2014, and Japanese Application No. 2014-223725, filed Oct. 31, 2014, the entire contents of the aforementioned applications are hereby incorporated herein by reference.

TECHNICAL FIELD

The present invention relates to a method of manufacturing a water-absorbent resin forming an absorbent material suitably used for hygienic materials such as disposable diapers and sanitary articles, a water-absorbent resin and a water-absorbing agent and an absorbent article using such a water-absorbent resin.

BACKGROUND ART

In recent years, water-absorbent resins have been widely used in the fields of hygienic materials such as sanitary articles and disposable diapers.

For water-absorbent resins as described above, cross-linked products of partially neutralized polymers of acrylic acid are preferred because they have many advantages, including the followings: they have excellent water-absorption performance; their raw materials such as acrylic acid has easy industrial availability, and therefore they can be manufactured with stable quality and low cost; and they show no shortcomings in which, for example, decomposition and degradation are likely to occur.

Examples of the desirable property of a water-absorbent resin in hygienic materials such as sanitary articles and disposable diapers include a high water-absorption capacity and an excellent water-absorption rate. However, for example, since a water-retention capacity and a water-absorption rate have a conflicting relationship, it is difficult to satisfy a balance between these properties.

As technologies for enhancing the properties of the water-absorbent resin suitably used for hygienic materials, for example, the following technologies are known: a method of performing reverse phase suspension polymerization using specific amounts of specific polymer protective colloid and surfactant (see Patent Document 1); a method of performing reverse phase suspension polymerization in multiple steps of two or more steps (see Patent Document 2); a method of performing reverse phase suspension polymerization under the coexistence of β-1,3-glucans to obtain a water-absorbent resin, and furthermore adding a crosslinking agent to the obtained water-absorbent resin to perform a crosslinking reaction (see Patent Document 3); a method of performing reverse phase suspension polymerization using a specific amount of persulfate using as a polymerization initiator (see Patent Document 4); and a method of performing aqueous solution polymerization in the presence of a phosphorous acid and/or a salt thereof to obtain a water-absorbent resin precursor, thereafter mixing the water-absorbent resin precursor and a surface-crosslinking agent and heating them (see Patent Document 5).

However, the water-absorbent resins obtained in these methods do not necessarily satisfy the high water-absorption capacity and the excellent water-absorption rate described above, and there are still improvements to be made.

In an absorbent material containing a water-absorbent resin, when the water-absorbent resin in which the diffusion property of a member to be absorbed is low is used, in the vicinity of the position of supply of a liquid to be absorbed, the water-absorbent resin, locally absorbs the liquid to be absorbed, and the swelled water-absorbent resin becomes dense, with the result that the blocking of the liquid often occurs. In this case, since the gelled water-absorbent resin further inhibits the diffusion property, the amount of re-wet of liquid to be absorbed tends to be increased.

PRIOR ART DOCUMENT

Patent Documents

Patent Document 1: Japanese Unexamined Patent Application, Publication No. H06-345819
Patent Document 2: Japanese Unexamined Patent Application, Publication No. H03-227301
Patent Document 3: Japanese Unexamined Patent Application, Publication No. H08-120013
Patent Document 4: Japanese Unexamined Patent Application, Publication No. H06-287233
Patent Document 5: Japanese Unexamined Patent Application, Publication No. H09-124710

DISCLOSURE OF THE INVENTION

Problems to be Solved by the Invention

The present invention is proposed in view of the foregoing situations, and has an object to provide a method of manufacturing a water-absorbent resin that is used in a hygienic material, that has an appropriate BET specific surface area and that is used as an absorbent material to enhance the performance of the absorbent material, a water-absorbent resin, a water-absorbing agent containing its resin, and an absorbent article that uses an absorbent material containing its resin.

Means for Solving the Problems

The present inventors have performed thorough studies to solve the problems described above. Consequently, they nave found that when reverse phase suspension polymerization of two steps or more is performed on a water-soluble ethylenically unsaturated monomer in a hydrocarbon dispersion medium in the presence of an azo compound and a peroxide, the BET specific surface area of secondary particles formed by the agglomeration of primary particles obtained by performing, at the time of polymerization of the first step, polymerization through adjustment of the used amount of internal-crosslinking agent in a specific range is controlled to fail within a specific range, with the result that the performance of an absorbent material using the water-absorbent resin is enhanced. Hence, the present invention has been completed. Specifically, the present invention provides the followings.

(1) The present invention provides a method of manufacturing a water-absorbent resin, wherein when reverse phase suspension polymerization of two steps or more is performed on a water-soluble ethylenically unsaturated monomer in a hydrocarbon dispersion medium in presence of at least an azo compound, a peroxide and an internal-crosslinking agent, the used amount of the internal-crosslinking agent at the time of the polymerization of a first step for 1 mole of the water-soluble ethylenically unsaturated monomer used at the time of the polymerization of the first step is adjusted to fall within a range of 0.015 to 0.150 mmol and the polymerization is performed such that a BET specific surface area of secondary particles formed by agglomeration of primary particles obtained is controlled.

(2) According to the present invention, in the invention of item (1) above, in the method of manufacturing a water-absorbent resin, the used amount (mole) of the internal-crosslinking agent at the time of the polymerization of the second and later steps for 1 mole of the water-soluble ethylenically unsaturated monomer of the second and later steps, is 90% or less of a used amount (mole) of the internal-crosslinking agent used at the time of the polymerization of the first step for 1 mole of the water-soluble ethylenically unsaturated monomer used at the time of the polymerization of the first step.

(3) According to the present invention, in the invention of item (1) or (2) above, in the method of manufacturing a water-absorbent resin, the BET specific surface area of the secondary particles that are formed by agglomeration of the primary particles and that are classified into 300 to 400 µm is controlled to be less than 0.03 $m^2$/g.

(4) The present invention provides a water-absorbent resin that is obtained, by polymerizing a water-soluble ethylenically unsaturated monomer in presence of an internal-crosslinking agent, where a water-absorption rate of physiological saline in the water-absorbent resin is 40 to 80 seconds, a mass proportion of particles from 150 to 850 µm, in the entire water-absorbent resin is 85 mass % or more, and a mass proportion of particles from 300 to 400 µm is 20 mass % or more and a BET specific surface area of particles classified into 300 to 400 µm is less than 0.03 $m^2$/g.

(5) According to the present invention, in the invention of item (4) above, in the water-absorbent resin, a median particle diameter of the water-absorbent resin is 200 to 600 µm.

(6) The present invention provides a water-absorbing agent that is obtained by mixing the water-absorbent resin according to item (4) or (5) above with an inorganic fine powder.

(7) The present invention provides an absorbent article that is formed by using an absorbent material containing the water-absorbent resin, according to item. (4) or (5) above.

(8) The present invention provides an absorbent article that is formed by using an absorbent material containing the water-absorbing agent according to item (6) above.

Effects of the Invention

By the method of manufacturing a water-absorbent resin according to the present invention, it is possible to obtain a water-absorbent resin having a BET specific surface area in an appropriate range.

In the water-absorbent resin according to the present invention, without the diameter of the particles thereof being increased, a water-absorption rate that is one of the factors for the diffusion and the re-wet of a liquid to be absorbed fails within an appropriate range, and the BET specific surface area thereof also falls within an appropriate range.

BRIEF DESCRIPTION OF THE DRAWINGS

FIG. 1 is a pattern diagram showing the schematic arrangement of an apparatus for measuring a water-absorption capacity of physiological saline under a load of 4.14 kPa.

PREFERRED MODE FOR CARRYING. OUT THE INVENTION

The present invention will be described in detail below.
1. Method of Manufacturing Water-absorbent Resin
A method of manufacturing a water-absorbent resin according to the present invention will be described.

The method of manufacturing a water-absorbent resin according to the present invention includes a step of performing, in a method of manufacturing a water-absorbent resin by performing reverse phase suspension polymerization on a water-soluble ethylenically unsaturated monomer in a hydrocarbon dispersion medium, the reverse phase suspension polymerization, in, the presence of an internal-crosslinking agent, and in the presence of an are based compound and a peroxide. A more detailed description will be given below.
Polymerization Step
[Water-soluble Ethylenically Unsaturated Monomer]

Water-soluble ethylenically unsaturated monomers include, for example, (meth)acrylic acid ("(meth)acry" herein refers to both "acry" and "methacry". The same shall apply hereinafter) and salts thereof; 2-(meth)acrylamide-2-methylpropanesulfonic acid and salts thereof; nonionic monomers such as (meth)acrylamide, N,N-dimethyl(meth)acrylamide, 2-hydroxyethyl(meth)acrylate, N-methylol(meth)acrylamide, polyethylene glycol mono(meth)acrylate; amino group-containing unsaturated monomers such as N,N-diethylaminoethyl(meth)acrylate, N,N-diethylaminopropyl(meth)acrylate, diethylaminopropyl(meth)acrylamide and quaternary compounds thereof. Among these water-soluble ethylenically unsaturated monomers, (meth)acrylic acid or salts thereof, (meth)acrylamide, N,N-dimethylacrylamide are preferred in view of easy industrial availability, and (meth)acrylic acid and salts thereof are more preferred. Note that these water-soluble ethylenically unsaturated monomers may be used alone or in combination of two or more.

Among these, acrylic acid and salts thereof are widely used as raw materials for water-absorbent resins, and may also be used in a case where the aforementioned water-soluble ethylenically unsaturated monomers are copolymerized with these partially neutralized acrylates. In this case, a partially neutralized acrylate is preferably used as a main water-soluble ethylenically unsaturated monomer in an amount of 70 to 100 mol % relative to the total amount of water-soluble ethylenically unsaturated monomers.

Preferably, a water-soluble ethylenically unsaturated monomer is dispersed in a hydrocarbon dispersion medium in the state of an aqueous solution, and subjected to reverse phase suspension polymerization. A water-soluble ethylenically unsaturated monomer in the form of an aqueous solution can increase the dispersion efficiency in a hydrocarbon dispersion medium. For the concentration of a water-soluble ethylenically unsaturated monomer in the aqueous solution, it is preferably in a range from 20 mass % to the saturation concentration. Since as will be described later, in polymerization in the presence of an azo compound, a polymerization rate tends to be increased, in view of avoiding the storage of excessive heat and easily obtaining the performance of the water-absorbent resin according to the present invention, the concentration of the water-soluble ethylenically unsaturated monomer is more preferably 55 mass % or less, further preferably 50 mass % or less and further more preferably 45 mass % or less. On the other hand, in order to maintain the productivity in a satisfactory level, the concentration of the water-soluble ethylenically unsaturated monomer is more preferably 25 mass % or more, and further preferably 28 mass % or more and further more preferably 30 mass % or more.

When a water-soluble ethylenically unsaturated monomer has an acid group like as (meth)acrylic acid, 2-(meth)acrylamide-2-methylpropanesulfonic acid, those having the acid group pre-neutralized with an alkaline neutralizer may be used if desired. Such alkaline neutralizers include alkali metal salts such as sodium hydroxide, sodium carbonate, sodium hydrogen carbonate, potassium hydroxide, potassium carbonate; ammonia and the like. Further, these alkaline neutralizers may be used in the form of an aqueous solution in order to simply neutralization procedures. Note that the aforementioned alkaline neutralizers may be used alone or in combination of two or more.

For the degree of neutralization of a water-soluble ethylenically unsaturated monomer with an alkaline neutralizer, the degree of neutralization of all acid groups in the water-soluble ethylenically unsaturated monomer is preferably 10 to 100 mol %, more preferably 30 to 90 mol %, further preferably 40 to 85 mol % and further more preferably 50 to 80 mol %.

[Hydrocarbon Dispersion Media]

Hydrocarbon dispersion. media include, for example, aliphatic hydrocarbons having 6 to 8 carbon atoms such as n-hexane, n-heptane, 2-methylhexane, 3-methylnexane, 2,3-dimethylpentane, 3-ethylpentane, n-octane; alicyclic hydrocarbons such as cyclohexane, methylcyclohexane, cyclopentane, methylcyclopentane, trans-1,2-dimethylcyclopentane, cis-1,3-dimethylcyclopentane, trans-1,3-dimethylcyclopentane; aromatic hydrocarbons such as benzene, toluene, xylene and the like. Among these hydrocarbon dispersion media, in particular, n-hexane, n-heptane, cyclohexane are suitably used in view of easy industrial availability, stable quality and low cost. These hydrocarbon dispersion media may be used alone or in combination of two or more. Note that examples of a mixture of hydrocarbon dispersion media include commercially available products such as EXXSOL heptane (made by Exxon Mobil Corporation: 75 to 85 mass % of heptane and its isomeric hydrocarbons thereof are contained), which can also produce a suitable result.

For the used amount of the hydrocarbon dispersion medium, it is preferably 100 to 1500 parts by mass relative to 100 parts by mass of a first-step water-soluble ethylenically unsaturated monomer, and more preferably 200 to 1400 parts by mass form the viewpoint that the water-soluble ethylenically unsaturated monomer can be uniformly dispersed to allow easy control over polymerization temperature. Note that as described below, reverse phase suspension polymerization is performed in multiple steps such as two or more steps, and the first-step polymerization described above means a polymerization reaction of the first step in multiple-step polymerization (The same shall apply hereinafter).

[Dispersion Stabilizer]

(Surfactant)

In the reverse phase suspension polymerization, in order for dispersion stability in the hydrocarbon dispersion medium of the water-soluble ethylenically unsaturated monomer to be enhanced, a dispersion stabilizer can also be used. A surfactant can be used as the dispersion stabilizer.

As surfactants, the followings may be used for example, sucrose fatty acid ester, polyglycerin fatty acid, sorbitan fatty acid ester, polyoxyethylene sorbitan fatty acid ester, polyoxyethylene glycerine fatty acid ester, sorbitol fatty acid ester, polyoxyethylene sorbitol fatty acid ester, polyoxyethylene alkyl ether, polyoxyethylene alkyl phenyl ether, polyoxyethylene castor oil, polyoxyethylene hydrogenated castor oil, alkyl allyl formaldehyde condensed polyoxyethylene ether, polyoxyethylene polyoxypropylene block copolymer, polyoxyethylene polyoxy propyl alkyl ether, polyethylene glycol fatty acid ester, alkyl glucoside, N-alkyl dlucohamide, polyoxyethylene fatty acid amide, polyoxyethylene alkylamine, phosphate ester of polyoxyethylene alkyl ether, phosphate ester of polyoxyethylene alkyl aryl ether and the like. Among these surfactants, in particular, sorbitan fatty acid ester, polyglycerin fatty acid ester, sucrose fatty acid ester are preferably used in view of dispersion stability of monomers. These surfactants may be used alone or in combination of two or more.

For the used amount of the surfactant, it is preferably 0.1 to 30 parts by mass relative to 100 parts by mass of a first-step water-soluble ethylenically unsaturated monomer, and more preferably 0.3 to 20 parts by mass.

(Polymeric Dispersion Agent)

A polymeric dispersion, agent may also be used, along with a surfactant described above, as a dispersion stabilizer used in the reverse phase suspension polymerization.

Polymeric dispersion agents include, for example, maleic anhydride modified polyethylene, maleic anhydride modified polypropylene, maleic anhydride modified ethylene-propylene copolymer, maleic anhydride modified EPDM (ethylene-propylene-diene-terpolymer), maleic anhydride modified polybutadiene, maleic anhydride-ethylene copolymer, maleic anhydride propylene copolymer, maleic anhydride-ethylene-propylene copolymer, maleic anhydride-butadiene copolymer, polyethylene, polypropylene, ethylene-propylene copolymer, oxidized polyethylene, oxidized polypropylene, oxidized ethylene-propylene copolymer, ethylene-acrylate copolymer, ethyl cellulose, ethyl hydroxyethyl cellulose and the like. Among these polymeric dispersion agents, particularly in view of dispersion stability of monomers, maleic anhydride modified polyethylene, maleic anhydride modified polypropylene, maleic anhydride modified ethylene-propylene copolymer, maleic anhydride-ethylene copolymer, maleic anhydride-propylene copolymer, maleic anhydride-ethylene-propylene copolymer, polyethylene, polypropylene, ethylene-propylene copolymer, oxidized polyethylene, oxidized polypropylene, oxidized ethylene-propylene copolymer are preferably used. These polymeric dispersion agents may be used alone or in combination of two or more.

For the used amount of the polymeric dispersion agents, it is preferably 0.1 to 30 parts by mass relative to 100 parts by mass of a first-step water-soluble ethylenically unsaturated monomer, and more preferably 0.3 to 20 parts by mass

[Internal-crosslinking Agent]

The method of manufacturing a water-absorbent resin according to the present invention is characterized in that in the presence of internal-crosslinking agent, the used amount of internal-crosslinking agent used at the time of the polymerization of the first step thereof is adjusted to fall within a specific range, and reverse phase suspension polymerization is performed on a water-soluble ethylenically unsaturated monomer.

Examples of the internal-crosslinking agent include internal-crosslinking agents that can crosslink the polymer of water-soluble ethylenically unsaturated monomers to be used. They include, for example, unsaturated polyesters obtained by reacting a polyol including a diol and a triol such as (poly)ethylene glycol ("(poly)" refers to a case where a prefix "poly" exists and a case where the prefix does not exist. The same shall apply hereinafter), (poly)propylene glycol, 1,4-butane diol, trimethylolpropane and (poly) glycerin with an unsaturated acid such as (meth)acrylic acid, maleic acid and fumaric acid; bisacrylamides such as N,N-methylenebisacrylamide; di(meth)acrylic acid esters or tri (meth)acrylic acid esters obtained by allowing polyepoxide to react with (meth)acrylic acid; di(meth)acrylic acid carbamyl esters obtained by allowing polyisocyanate such as tolylene diisocyanate, hexamethylene diisocyanate to react with (meth)acrylic acid hydroxyethyl; compounds having two or more polymerizable unsaturated groups, for example, allylated, starch, alkylated cellulose, diallyl phthalate, N,N', N"-triallylisocyanate, divinylbenzene and the like; polyglycidyl compounds, for example, diglycidyl compounds such as (poly)ethylene glycol diglycidyl ether, (poly)propylene glycol diglycidyl ether, (poly)glycerin diglycidyl ether, triglycidyl compounds and the like; epihalohydrin compounds such as epichlorohydrin, epibromhydrin, α-methyl epichlorohydrin; compounds having two or more reactive functional groups, for example, isocyanate compounds such as 2,4-tolylene diisocyanate, hexamethylene diisocyanate; oxetane compounds such as 3-methyl-3-oxetane methanol, 3-ethyl-3-oxetane methanol, 3-butyl-3-oxetane methanol, 3-methyl-3-oxetane ethanol, 3-ethyl-3-oxetane ethanol, 3-butyl-3-oxetane ethanol. Among these internal-crosslinking agents, polyglycidyl compounds is preferably used, and diglycidyl compounds such as (poly)ethylene glycol diglycidyl ether, (poly)propylene glycol diglycidyl ether, (poly) glycerin diglycidyl ether are particularly preferably used. These internal-crosslinking agents may be used alone or in combination of two or more.

In order for the obtained polymer to indicate an excellent water-absorption performance by appropriate crosslinking, the used amount of internal-crosslinking agent at the time of the polymerization of the first step for 1 mole of the water-soluble ethylenically unsaturated monomer used at the time of the polymerization of the first step is 0.015 mmol or more, preferably 0.020 mmol or more and more preferably 0.025 mmol or more. The used amount of internal-crosslinking agent at the time of the polymerization of the first step for 1 mole of the water-soluble ethylenically unsaturated monomer used at the time of the polymerization of the first step is 0.150 mmol or less, preferably 0.120 mmol or less and more preferably 0.100 mmol or less. Hence, the used amount of internal-crosslinking agent at the time of the polymerization of the first step for 1 mole of the water-soluble ethylenically unsaturated monomer used at the time of the polymerization of the first step is 0.015 to 0.150 mmol, preferably 0.020 to 0.120 mmol and more preferably 0.025 to 0.100 mmol.

When in the polymerization of the second and the later steps, the internal-crosslinking agent is used more than necessary, there may be possibility that a water absorbent resin having an appropriate water-absorption rate is not obtained. Hence, in the second and the later steps, the used amount (mole) of internal-crosslinking agent for 1 mole of the water-soluble ethylenically unsaturated monomer of the second and the later steps is preferably 90% or less of the used amount (mole) of internal-crosslinking agent used at the time of the polymerization of the first step for 1 mole of the water-soluble ethylenically unsaturated monomer used at the time of the polymerization of the first step, and more preferably 10 to 85% of the used amount (mole).

[Azo Based Compound and Peroxide]

The method of manufacturing a water-absorbent resin according to the present invention is characterized in that reverse phase suspension polymerization is performed on the water-soluble ethylenically unsaturated monomer in the presence of an azo based compound and a peroxide.

In the above polymerization step, the phrase "in the presence of an azo based compound and a peroxide" does not necessarily means that the azo based compound and the peroxide are coexistent at the beginning of a polymerization reaction, but means that the other compound is present before a monomer conversion ratio by radical cleavage due to one compound becomes less than 10%. However, the both are preferably present in an aqueous solution containing a water-soluble ethylenically unsaturated monomer before the start of the polymerization reaction. Further, an azo based compound and a peroxide may be added to a polymerization reaction system via different flow channels or may be sequentially added to the polymerization reaction system via the same flow channel.

Note that an arc based compound and a peroxide to be used may be in the form of powder or an aqueous solution.
(Azo Based Compound)

Specifically, azo based compounds include, for example, those azo based compounds such as 1-{(1-cyano-1-methylethyl)azo}formamide, 2,2'-azobis[2-(N-phenylamidino) propane]dihydrochloride, 2,2'-azobis{2-[N-(4-chlorophenyl)amidino]propane}dihydrochloride, 2,2'-azobis{2-[N-(4-hydroxyphenyl)amidino]propane}dihydrochloride, 2,2'-azobis[2-(N-benzyl amidino)propane]dihydrochloride, 2,2'-azobis[2-(N-allyl amidino)propane]dihydrochloride, 2,2'-azobis(2-amidinopropane) dihydrochloride, 2,2'-azobis{2-[N-(2-hydroxyethyl)amidino]propane}dihydrochloride 2,2'-azobis[2-(5-methyl-2-imidazoline-2-yl)propane] dihydrochloride, 2,2'-azobis[2-(2-imidazoline-2-yl) propane]dihydrochloride, 2,2'-azobis[2-(4,5,6,7-tetrahydro-1H-1,3-diazepine-2-yl)propane]dihydrochloride, 2,2'-azobis [2-(5-hydroxy-3,4,5,6-tetrahydro-pyrimidine-2-yl)propane] dihydrochloride, 2,2'-azobis{2-[1-(2-hydroxyethyl)-2-imidazoline-2-yl]propane}dihydrochloride 2,2'-azobis[2-(2-imidazoline-2-yl)propane], 2,2'-azobis{2-methyl-N-[1,1-bis (hydroxymethyl)-2-hydroxyethyl]propionamide}, 2,2'-azobis (2-methyl-N-[1,1-bis(hydroxymethyl)ethyl] propionamide 2,2'-azobis[2-methyl-N-(2-hydroxyethyl) propionamide], 2,2'-azobis(2-methylpropionamide) dihydrochloride, 4,4'-azobis-4-cyanovaleinic acid, 2,2'-azobis[2-(hydroxymethyl)propionitrile], 2,2'-azobis[2-(2-imidazoline-2-yl)propane]disulfate dihydrate, 2,2'-azobis [N-(2-carboxyethyl)-2-methylpropione amidine] tetrahydrate, 2,2'-azobis[2-methyl-N-(2-hydroxyethyl) propionamide]. Among these, 2,2'-azobis(2-amidinopropane)dihydrochloride, 2,2'-azobis{2-[1-(2-hydroxyethyl)-2-imidazoline-2yl]propane}dihydrochloride, 2,2'-azobis-[N-(2-carboxyethyl)-2-methylpropione amidine]tetrahydrate are particularly preferred because it is easy to adjust a polymerization reaction such as a polymerization temperature and it is possible to obtain a water-absorbent resin having an excellent water-absorption performance. These azo compounds may be used alone or in combination of two or more.

(Peroxide)

Peroxides include, for example, persulfates such as potassium persulfate, ammonium persulfate, sodium persulfate; peroxides such as methyl ethyl ketone peroxide, methyl isobutyl ketone peroxide, di-t-butyl peroxide, t-butyl cumyl peroxide, t-butyl peroxyacetate, t-butyl peroxy isobutyrate, t-butyl peroxy pivalate, hydrogen peroxide. Among these peroxides, in view of obtaining a water-absorbent resin having an excellent water-absorption performance, potassium persulfate, ammonium persulfate, sodium persulfate, hydrogen peroxide are preferably used, and further, potassium, persulfate, ammonium persulfate, sodium persulfate are more preferably used. These peroxides may be used alone or in combination of two or more.

(Used Amount and Used Proportion of Azo Based Compound and Peroxide)

For the used amount of an azo based compound and a peroxide, in view of reducing the time of the polymerization reaction, is preferably 0.00005 mol or more relative to 1 mol of a water soluble ethylenically unsaturated monomer, more preferably 0.0001 mol or more. Further, in view of preventing a rapid polymerization reaction, the used amount is preferably 0.005 mol or less relative to 1 mol of a water-soluble ethylenically unsaturated monomer, and more preferably 0.001 mol or less.

For the used proportion of an azo based compound and a peroxide, the proportion of an azo based compound is preferably 40 mass % or more in. the total used amount of an azo based compound and a peroxide, more preferably 50 mass % or more, further preferably 60 mass % or more and further more preferably 70 mass % or more. On the other hand, the proportion of an azo based compound is preferably 95 mass % or less in the total used amount of an azo based compound and a peroxide, more preferably 90 mass % or less, further preferably 85 mass % and further more preferably 80 mass % or less. The mass ratio range (azo based compound : peroxide) is preferably 8:12 to 19:1.

[Other Components]

In the method of manufacturing a water-absorbent resin according to the present invention, other components may be added to an aqueous solution containing a water-soluble ethylenically unsaturated monomer to perform reverse phase suspension polymerization if desired. As other components, chain transfer agents, thickeners, other various additives and the like may be added.

(Chain Transfer Agent)

In the method of manufacturing a water-absorbent resin according to the present invention, in order to control the water-absorption performance of the water-absorbent resin, polymerization may be performed on the water-soluble ethylenically unsaturated monomer in the presence of a chain transfer agent.

Specific examples of the chain transfer agent include: thiols such as ethane thiol, propane thiol and dodecanethiol; thiol acids such as thioglycolic acid, thiomalic acid, dimethyl dithiocarbamate, diethyl dithiocarbamate and salts thereof; secondary alcohols such as isopropanol; phosphorous acid compounds, such as normal salts of phosphorous acid (for example, as phosphorous acid, phosphorous acid disodium, dipotassium phosphite and phosphorous acid diammonium, etc.), and such as acidic salts of phosphorous acid (for example, as sodium hydrogen phosphite, potassium hydrogen phosphite and phosphorous acid ammonium hydrogen, etc.); phosphoric acid compounds, such as normal salts of phosphoric acid (for example, as phosphoric acid, sodium phosphate, potassium phosphate and ammonium phosphate, etc.), and such as acid salts of phosphoric acid (for example, as sodium dihydrogen phosphate, potassium dihydrogen phosphate, ammonium dihydrogen phosphate, disodium hydrogen phosphate, potassium hydrogen phosphate dibasic and diammonium hydrogen phosphate, etc.); hypophosphorous acid compounds such as hypophosphorous acid salts (for example, as hypophosphorous acid, sodium hypophosphite, potassium hypophosphite and ammonium hypophosphite, etc.); pyrophosphoric acid, tripolyphosphate, polyphosphoric acid and the salts thereof; and trimethyl phosphate, nitrilotrimethylene triphosphonic acid and the like. These chain transfer agents may be used alone or in combination of two or more. As the chain transfer agent, the hydrate thereof may be used.

For one mole of the water-soluble ethylenically unsaturated monomer, the used amount of chain transfer agent is preferably 0.00001 to 0.0005 mol, and is more preferably 0.000025 to 0.00012 mol.

(Thickener)

In the method of manufacturing a water-absorbent resin according to the present invention, a thickener may be added to an aqueous solution containing a water-soluble ethylenically unsaturated monomer to perform reverse phase suspension polymerization. By adding a thickener to adjust the viscosity of an aqueous solution, the median particle diameter obtained by reverse phase suspension polymerization can also be controlled.

Specifically, as a thickener, for example, hydroxyethyl cellulose, hydroxypropyl cellulose, methyl cellulose, carboxymethyl cellulose, polyacrylic acid, (partially) neutralized polyacrylic acid, polyethylene glycol, polyacrylamide, polyethyleneimine, dextrin, sodium alginate, polyvinyl alcohol, polyvinyl pyrrolidone, polyethylene oxide and the like can he used. Note that in a case where the stirring speeds at the time of polymerization are the same, there is a tendency that the higher the viscosity of an aqueous solution of a water-soluble ethylenically unsaturated monomer is, the larger the median particle diameter of the resulting particles is.

[Reverse Phase Suspension Polymerization]

When performing reverse phase suspension polymerization, for example, a water-soluble ethylenically unsaturated monomer is dispersed in a hydrocarbon dispersion medium in the presence of a surfactant and/or a polymeric dispersion agent. When doing this, a surfactant and a polymeric dispersion agent may be added either before or after the aqueous monomer solution is dispersed as long as they are added before starting a polymerization reaction.

In particular, in a view of easy reduction of the amount of a residual hydrocarbon dispersion medium in the resulting water-absorbent resin, it is preferred that polymerization is performed after a water-soluble ethylenically unsaturated monomer is added and then dispersed in a hydrocarbon dispersion medium in which a polymeric dispersion agent has been dispersed, and then a surfactant is further dispersed.

In the present invention, the reverse phase suspension polymerization is performed in multiple steps of two or more steps. In the method of manufacturing a water-absorbent resin according to the present invention, the polymerization of two or more steps as described above is performed, and thus a water-absorbent resin containing secondary particles in which primary particles are agglomerated is manufactured. Further, in view of increased productivity, it is more preferably performed in 2 or 3 steps.

In a case where reverse phase suspension polymerization is performed in multiple steps such as two or more steps, after a first-step reverse phase suspension polymerization is performed, a water-soluble ethylenically unsaturated monomer can be added to the reaction mixture obtained in the first-step polymerization reaction, and mixed to perform a second step reverse phase suspension polymerization as in the first step. Preferably, in a case of reverse phase suspension polymerization, at each step of the second step and later steps, reverse phase suspension polymerization may be performed by adding, in addition to a water-soluble ethylenically unsaturated monomer, an internal-crosslinking agent, an azo compound and a peroxide described above within the aforementioned range of the molar ratio of each component relative to the water-soluble ethylenically unsaturated monomer on the basis of the amount of the water-soluble ethylenically unsaturated monomer to be added in the reverse phase suspension polymerization in each step of the second step and later steps. In the method of manufacturing a water-absorbent resin according to the present invention, in the polymerization of the second step and the subsequent steps, the polymerization is performed in the presence of an azo compound and a peroxide.

For the reaction temperature for a polymerization reaction, it is preferably 20 to 110° C., more preferably 40 to 90° C. from the viewpoint that profitability may be improved by allowing rapid progress of a polymerization to reduce a polymerization time, and polymerization heat may be easily removed to perform a smooth reaction. Further, the reaction time is preferably 0.5 to 4 hours.

An operation of stirring the aqueous monomer solution can be performed with various known stirring blades. Specifically, as the stirring blade, for example, a propeller blade, a paddle blade, an anchor blade, a turbine blade, a Pfaudler blade, a ribbon blade, a FULLZONE blade (made by Shinko Pantec Co., Ltd.), a MAXBLEND blade (made by Sumitomo Heavy Industries, Ltd.), a Super-Mix blade (Satake Chemical Machinery Industry Co., Ltd.) or the like can be used. In the present invention, an stirring speed at the time of the polymerization reaction of the water-soluble ethylenically unsaturated monomer, for example, the number of revolutions of stirring, is adjusted, and thus the median particle diameter of primary particles obtained by the reverse phase suspension polymerization of the first step is controlled, with the result that it is possible to efficiently control the BET specific surface area of second particles formed by the agglomeration of the primary particles. With the same type of stirring blade, the median particle diameter of the primary particles obtained more as the stirring speed is increased tends to be decreased.

In the method of manufacturing a water-absorbent resin according to the present invention, it is possible to obtain a water-containing gel in the form of moderately sized particle, consequently it is possible to easily obtain a fine-grained water-absorbent resin in the form of moderately sized particle suitable for the preparation of an absorbent article.

Post-crosslinking Step

Next, in the water-absorbent resin according to the present invention, post-crosslinking (post-crosslinking reaction) is preferably performed with a post-crosslinking agent on a hydrous gel-like material having an internal-crosslinking structure obtained by performing the reverse phase suspension polymerization on the water-soluble ethylenically unsaturated monomer, as described above, in the presence of the internal-crosslinking agent, and in the presence of an azo compound and a peroxide. Thus, after the polymerization, the post-crosslinking reaction is performed on the hydrogel having an internal-crosslinking structure, and thus it is possible to obtain a water-absorbent resin particularly suitable for the applications of hygienic materials in which a crosslinking density in the vicinity of the surface of the water-absorbent resin is increased to enhance various types of performance such as a water-absorption capacity under a load, an absorption rate and a gel strength.

Specifically, post-crosslinking agents can include those compounds having two or more reactive functional groups. They include, for example, polyols such as ethylene glycol, propylene glycol, 1,4-butanediol, trimethylolpropane, glycerin, polyoxyethylene glycol, polyoxypropylene glycol, polyglycerin; polyglycidyl compounds such as (poly) ethylene glycol diglycidyl ether, (poly) glycerin diglycidyl ether, (poly)glycerin triglycidyl ether, trimethylolpropane triglycidyl ether, (poly)propylene glycol polyglycidyl ether, (poly)glycerol polyglycidyl ether; haloepoxy compounds such as epichlorohydrin, epibromhydrin, α-methyl epichlorohydrin; isocyanate compounds such as 2,4-tolylene diisocyanate, hexamethylene diisocyanate; oxetane compounds such as 3-methyl-3-oxetane methanol, 3-ethyl-3-oxetane methanol, 3-butyl-3-oxetane methanol, 3-methyl-3-oxetane ethanol, 3-ethyl-3-oxetane ethanol, 3-butyl-3-oxetane ethanol; oxazoline compounds such as 1,2-ethylenebisoxazoline; carbonate compounds such as ethylene carbonate; hydroxyalkylamide compounds such as bis[N,N-di(β-hydroxyethyl)]adipamide. Among these post-crosslinking agents, particularly preferred are polyglycidyl compounds such as (poly)ethylene glycol diglycidyl ether, (poly)glycerin diglycidyl ether, (poly)glycerol triglycidyl ether, trimethylolpropane triglycidyl ether, (poly)propylene glycol polyglycidyl ether, (poly)glycerol polyglycidyl ether. These post-crosslinking agents may be used alone or in combination of two or more.

The used amount of a post-crosslinking agent is preferably 0.00001 to 0.01 mol relative to 1 mol of the total amount of a water-soluble ethylenically unsaturated monomer used for polymerization, more preferably 0.00005 to 0.005 mol and further preferably 0.0001 to 0.002 mol.

As a method of adding a post-crosslinking agent, the post-crosslinking agent may be added as it is or as an aqueous solution. A post-crosslinking agent may also be added as a solution in which a hydrophilic organic solvent is used as a solvent if desired. Hydrophilic organic solvents include, for example, lower alcohols such as methyl alcohol, ethyl alcohol, n-propyl alcohol, isopropyl alcohol; ketones such as acetone, methyl ethyl ketone; ethers such as diethyl ether, dioxane, tetrahydrofuran; amides such as N,N-dimethylformamide; sulfoxides such as dimethyl sulfoxide. These hydrophilic organic solvents may be used alone, in combination of two or more, or in admixture with water.

As for the timing when a post-crosslinking agent is added, it can be added as long as the polymerization reaction of water-soluble ethylenically unsaturated monomers has been almost completed, but it is preferably added in the presence of water in the range of 1 to 400 parts by mass relative to 100 parts by mass of a water-soluble ethylenically unsaturated monomer, more preferably added in the presence of water in the range of 5 to 200 parts by mass, further preferably added in the presence of water in the range of 10 to 100 parts by mass and yet still further more preferably added in the presence of water in the range of 20 to 60 parts by mass. Note that the amount of water means the total amount of a water content in a polymerization system and a water content used if desired when adding a post-crosslinking agent.

For the reaction temperature in the post-crosslinking reaction, it is preferably 50 to 250° C., more preferably 60 to 180° C., further preferably 60 to 140° C. and further more preferably 70 to 120° C. Further, the reaction time of the post-crosslinking reaction is preferably 1 to 300 minutes, and more preferably 5 to 200 minutes.

Drying Step

In the method of manufacturing a water-absorbent resin according to the present invention, a drying step of removing water, a hydrocarbon dispersion medium and the like using distillation by applying energy such as heat from the outside after performing the aforementioned reversed phase suspension polymerization may be included. When performing dehydration of a hydrous gel after reversed phase suspension polymerization, a system in which the hydrous gel is dispersed in a hydrocarbon dispersion medium is heated to temporarily evaporate water and the hydrocarbon dispersion medium from the system by azeotropic distillation. At this time, only the hydrocarbon dispersion medium evaporated is allowed to return into the system, enabling continuous azeotropic distillation. In that case, the temperature in the system during the drying treatment is maintained at or below the azeotropic temperature of the hydrocarbon dispersion medium. Therefore this is preferred from the view point that, for example, the resin is less susceptible to deterioration. Subsequently, water and the hydrocarbon dispersion medium is evaporated away to obtain particles of a water-absorbent resin. By controlling processing conditions of this drying step after polymerization to adjust the amount of dehydrated water, various properties of the resulting water-absorbent resin can be controlled.

In the drying step, the drying treatment may be performed by distillation under ordinary pressure or under reduced pressure. Further, the drying treatment may be performed under a gas flow of nitrogen and the like in view of increased drying efficiency. When performing the drying treatment under ordinary pressure, a drying temperature is preferably 70 to 250° C., more preferably 80 to 180° C., further preferably 80 to 140° C. and particularly preferably 90 to 130° C. Further, when performing the drying treatment under reduced pressure, a drying temperature is preferably 40 to 160° C., more preferably 50 to 110° C.

Note that in a case where post-crosslinking step is performed with a post-crosslinking agent after monomers are polymerized by reversed phase suspension polymerization as described above, drying step is performed by distillation as described above after the completion of the post-crosslinking step. Alternatively, the post-crosslinking step and the drying step may be performed simultaneously.

Further, if desired, various additives such as chelating agents, reducing agents, oxidizing agents, antibacterial agents, deodorizing agents may be added to a water-absorbent resin after polymerization step during or after drying step.

2. Water-absorbent Resin

The water-absorbent resin according to the present invention will then be described. For example the water-absorbent resin according to the present invention can be obtained by the method described above. Specifically, it can be obtained by performing polymerization while adjusting the used amount of internal-crosslinking agent at the time of the polymerization of the first step, its BET specific surface area is controlled to fall within an appropriate range and an absorbent article using the water-absorbent resin has an excellent water-absorption capacity.

Specifically, the water-absorbent resin according to the present invention is a water-absorbent resin that can be obtained by polymerizing a water-soluble ethylenically unsaturated monomer in the presence of an internal-crosslinking agent, the water-absorption rate of physiological saline is 40 to 80 seconds, the mass proportion of the particles from 150 to 850 µm in the entire water-absorbent resin is 85 mass % or more, the mass proportion of the particles from. 300 to 400 µm is 20 mass % or more and the BET specific surface area of the particles that are classified into 300 to 400 µm and are measured is less than 0.03 m$^2$/g.

The "water-absorption rate" of the water-absorbent resin here is a property that affects the properties required for such an absorbent material when the absorbent material is formed by combining the water-absorbent resin and a hydrophilic fiber, and for example, there is a tendency that the water-absorption rate is appropriately decreased to have an excellent diffusion property on the entire absorbent material of a liquid to be absorbed. The water-absorption rate of the water-absorbent resin can be measured based on the following method as the water-absorption rate of physiological saline.

Specifically, the measurement of the water-absorption rate is performed as follows. As described later in Examples, within a room conditioned at 25±1° C., 50±0.1 g of physiological saline adjusted at a temperature of 25±0.2° C. in a constant temperature water tank is stirred with a magnetic stirrer bar (8 mm φ×30 mm without a ring) at 600 rpm to produce vortex, 2.0±0.002 g of a water-absorbent resin that is a measurement sample is added into the physiological saline at a time and the time (in seconds) during which after the addition of the water-absorbent resin, the vortex is made to disappear and the liquid surface becomes flat is measured, with the result that the time can be assumed to be the water-absorption rate of the water-absorbent resin.

In the water-absorbent resin according to the present invention, the water-absorption rate of physiological, saline is 40 to 80 seconds. The water-absorption rate of physiological saline is preferably 42 seconds or more and is more preferably 45 seconds or more because when the water-absorbent resin, is used for an absorbent material, the absorbent material has a satisfactory diffusion property.

In the water-absorbent resin according to the present invention, the mass proportion of the particles from 150 to 850 µm in the entire water-absorbent resin is 85% or more, and such particle size distribution is provided, that the mass proportion of the particles from 300 to 400 µm is 20% or more.

With respect to the particle size distribution of the water-absorbent resin, the mass proportion of the particles from 150 to 850 µm in the entire water-absorbent resin is 85 mass % or more, and more preferably 90 mass % or more Furthermore, the mass proportion of the particles from 300 to 400 µm in the entire water-absorbent resin is 20 mass % or more, more preferably 25 mass % or more and further preferably 30 mass % or more.

In the water-absorbent resin according to the present invention, the median particle diameter is preferably 200 to 600 µm, more preferably 200 to 500 µm and further preferably 250 to 450 µm.

The water-absorbent resin is not limited to a water-absorbent resin formed with only secondary particles in which primary particles are agglomerated, and the water-absorbent resin may contain single particles (primary particles). Examples of the shape of the primary particle include a substantially spherical shape, an irregular pulverized shape and a plate shape. When primary particles are manufactured by reverse phase suspension polymerization, a substantially spherical single particle shape having a smooth surface shape such as a spherical shape or an oval spherical shape is present, and in the primary particles of such a shape, the surface shape is smooth, thus fluidity as powder is enhanced and the agglomerated particles are unlikely to be broken even when a shock is received because the agglomerated particles are densely packed with primary particles, with the result that the water-absorbent resin having a high particle strength is achieved.

In the water-absorbent resin according to the present invention, the BET specific surface area of the particles that are classified into 300 to 400 μm and are measured is less than 0.03 m$^2$/g. The BET specific surface area is preferably 0.028 m$^2$/g or less, and more preferably 0.026 m$^2$/g or less. The BET specific surface area is preferably 0.010 m$^2$/g or more. The BET specific surface area is made to fall within such a range, and thus it is possible to enhance its water-absorption performance when it is used for an absorbent article.

As described later in Examples, in the measurement of the BET specific surface area, the BET specific surface area can be determined as follows. The water-absorbent resin that is passed through a sieve of 400 μm openings and that is adjusted into particle diameters held on a sieve of 300 μm openings is used, this sample is dried under degassing conditions of thermal vacuum exhaust at 100° C. for 16 hours, thereafter by a method in which a specific surface area measurement apparatus (made by Quantachrome Co. Ltd. AUTOSORB-1) is used and Krypton gas is used as an adsorption gas, an adsorption isotherm is measured at a temperature of 77 K and the BET specific surface area can be determined from a multipoint BET plot.

When the BET specific surface area of a water-absorbing agent obtained by mixing an additive such as an inorganic fine powder to the water-absorbent resin is measured, if the BET specific surface area of the additive adhered to the surface of the water-absorbent resin is extremely large, it may be consequently likely to obtain such a measurement value that the water-absorbing agent has a large specific surface area. Hence, in order to measure<the BET specific surface area of the water-absorbent resin>described in the present specification, it is desirable to measure the water-absorbent resin before the addition of the additive or to measure, in the case of the water-absorbing agent, the water-absorbent resin after the removal of the additive adhered to the surface by washing.

In the water-absorbent resin according to the present invention, the water-retention capacity of physiological saline is preferably 30 g/g or more. The water-retention capacity of physiological saline refers to the mass of physiological saline that can be absorbed by the water-absorbent resin per unit mass, and indicates the degree of the absorption capacity of the liquid of the water-absorbent resin. The water-retention capacity of physiological saline is more preferably 35 g/g or more, and further preferably 40 g/g or more. The upper limit value of the water-retention capacity of physiological saline is preferably 60 g/g or less.

In the water-absorbent resin according to the present invention, the water-absorption capacity of physiological saline under a load of 4.14 kPa is preferably 16 ml /g or more, more preferably 18 mi/p or more and further preferably 20 ml/g or more. The upper limit of the water-absorption capacity of physiological saline under a load of 4.14 kPa is preferably 50 ml/g or less.

The water-retention capacity of physiological saline, the water-absorption capacity of physiological saline under a load of 4.41 kPa, the water-absorption rate of physiological saline, the median particle diameter and the BET specific surface area in the water-absorbent resin described above can he measured in a measurement method described in later in Examples.

In order to give various types of performance to the obtained water-absorbent resin, an additive corresponding to the purpose is mixed, with the result that it is possible to use it as a water-absorbing agent. Examples of such an additive include an inorganic fine powder, a surfactant, an oxidizing agent, a reducing agent, a metal chelating agent, a radical chain inhibitor, an antioxidant, an antibacterial agent and a deodorant. For example, 0.05 to 5 mass parts of an inorganic fine powder is added to 100 mass parts of the water-absorbent resin, and thus it is possible to obtain a water-absorbing agent whose fluidity is enhanced. Examples of the inorganic fine powder include hydrophilic silica, hydrophobic silica, talc, zeolite and aluminum oxide powder.

3. Absorbent Material and Absorbent Article

The water-absorbent resin according to the present invention forms, for example, the absorbent material used for hygienic materials such as sanitary articles and disposable diapers, and is preferably used for an absorbent article including the absorbent material.

Here, an absorbent material in which a water-absorbent resin is used comprises, for example, the water-absorbent resin and a hydrophilic fiber. The structures of the absorbent material include a dispersion mixture obtained by mixing a water-absorbent resin and a hydrophilic fiber to give a uniform composition, a sandwich structure in which a water-absorbent resin is sandwiched between layered hydrophilic fibers, a structure in which a water-absorbent resin and a hydrophilic fiber is wrapped in tissue and the like. Note that other components, for example, adhesive hinder such as thermal adhesive synthetic fibers, hot melt adhesives, adhesive emulsions for increasing the shape retention capability of an absorbent material may be included In the absorbent material.

For the content of a water-absorbent resin in an absorbent material. It is preferably 5 to 95 mass, more preferably 20 to 90 mass % and further preferably 30 to 80 mass %. When the content of a water-absorbent resin is less than 5 mass u, the absorption capacity of an absorbent material may be decreased, resulting in a leakage and re-wet of a liquid. On the other hand, when the content of a water-absorbent resin is more than 95 mass %, the cost of an absorbent material increases, and the touch of the absorbent material becomes harder.

Hydrophilic fibers include cellulose fibers such as cotton-like pulp obtained from wood, mechanical pulp, chemical pulp, semichemical pulp; artificial cellulose fibers such as rayon and acetate; fibers comprising synthetic resin such as hydrophilized polyamide, polyester, and polyolefine.

Moreover, an absorbent material in which a water-absorbent resin is used can be held between a liquid permeable sheet (top sheet) through which a liquid can permeate and a liquid impermeable sheet (back sheet) through which a liquid cannot permeate to give an absorbent article. The liquid permeable sheet is arranged on the side to be in contact with the body while the liquid impermeable sheet is arranged opposite to the side to be in contact with the body.

Liquid permeable sheets include non-woven and porous synthetic resin sheets of an air through type, a span bond type, a chemical bond type, a needle punch type and the like comprising fiber such as polyethylene, polypropylene, polyester and the like. Further, liquid impermeable sheets include synthetic resin films comprising a resin such as polyethylene, polypropylene, polyvinyl chloride and the like.

EXAMPLES

4. Example

Hereafter, the present invention will be described in detail with reference to Examples and Comparative Examples. However, the present invention shall not in any way be limited to the following Examples and the like.

4-1. Method for Evaluation Test

[Evaluation Test for Water-absorbent Resin]

Water-absorbent resins obtained from Examples 1 to 7, and Comparative Examples 1 to 4 below were subjected to various tests described below for evaluation. In the followings, each evaluation test method will be described.

(1) Water-retention Capacity of Physiological Saline

A cotton bag (Men Broad No. 60, horizontal 100 mm×vertical 200 mm) into which 2.0 g of a water-absorbent resin was weighed was placed within a beaker of 500 ml capacity 500 g of 0.9 mass % sodium chloride aqueous solution (physiological saline) was poured into the cotton bag including the water-absorbent resin at a time so as not to produce a lump, and the upper portion of the cotton bag was tied with a rubber band and was left still for 30 minutes, with the result that the water-absorbent resin was swollen. The cotton bag after the elapse of 30 minutes was dehydrated for one minute with a dehydrator (made by Kokusan Centrifuge Co., Ltd., product number: H-122) which was set that a centrifugal force was 167 G, and the mass Wa (g) of the cotton bag containing the dehydrated swollen gel was measured. The same operation was performed without addition of the water-absorbent resin, the empty mass Wb (g) of the wet cotton bag was measured and its water-retention capacity of physiological saline was calculated from formula below.

water-retention capacity of physiological saline $(g/g) = [Wa - Wb](g)/\text{mass of water-absorbent resin}(g)$ (2) Water-absorption Capacity of Physiological Saline Under a Load of 4.14 kPa A water-absorption capacity of physiological saline under a load of 4.14 kPa of a water-absorbent resin was measured using a measurement apparatus X. A schematic arrangement of the measurement apparatus X is shown in FIG. 1.

The measurement apparatus X shown in FIG. 1 comprises a buret part 1, a conduit 2, a measurement stage 3, a measurement part 4 placed on the measurement stage 3. In the buret part 1, a rubber stopper 14 is connected to the upper part of a buret 10, and an air introducing pipe 11 and a cock 12 is connected to the lower part of the buret 10. Further, cock 13 is attached to t part of the air introducing pipe 11. A conduit 2 connects the buret part 1 and the measurement stage 3. The diameter of the conduit 2 is 6 mm. The measurement stage 3 has a hole with a diameter of 2 mm at the center, to which the conduit 2 is connected. The measurement part 4 is provided with a cylinder 40 and a nylon mesh 41 patched on the bottom of the cylinder 40, as well as a weight 42. The inner diameter of the cylinder 40 is 2.0 cm. The nylon mesh 41 is formed as 200 mesh (75 μm openings). Further, it is configured such that a predetermined amount of a water-absorbent resin 5 is uniformly distributed on the nylon mesh 41. The weight 42 has a diameter of 19 cm and a mass of 119.6 g. The weight 42 is to be placed on the water-absorbent resin 5 to uniformly apply a load of 4.14 kPa to the water-absorbent resin 5.

Using the measurement apparatus X having a structure as described above, first, the cock 12 and the cock 13 at the buret part 1 were closed, and then physiological saline adjusted to 25° C. was introduced into the buret 10 from the top. Subsequently, the top of the buret was plugged with the rubber stopper 14, and then the cock 12 and the cock 13 at the buret part 1 were opened. Next, the height of the measurement stage 3 was adjusted so that the tip of the conduit 2 at the center of the measurement stage 3 is leveled with, the air inlet of the air introducing pipe 11.

Meanwhile, 0.10 g of the water-absorbent resin 5 was uniformly distributed on the nylon mesh 41 in the cylinder 40, and then the weight 42 was placed on that water-absorbent resin 5. The measurement part 4 was arranged so that its center coincided with the conduit inlet at the center of the measurement stage 3.

The amount of reduced physiological saline in the buret 10 (the amount of physiological saline absorbed by the water-absorbent resin 5) Wc (mL) was continuously measured from the time point when the water-absorbent resin 5 started to absorb water. At an elapsed time of 60 minutes from the start of water absorption, a water-absorption capacity of physiological saline under a load of 4.14 kPa of the water-absorbent resin was calculated by the following formula.

Water-absorption capacity of physiological saline under a load of 4.14 kPa (mL/g)=$Wc/0.10$ (g)

(3) Water-absorption Rate of Physiological Saline

The water-absorption rate of physiological saline was measured within a room whose temperature was adjusted at 25±1° C., 50±0.1 g of physiological saline adjusted at 25±0.2° C. in a constant temperature water tank was stirred with a magnetic stirrer bar (8 mm φ×30 mm without a ring) at 600 rpm to produce vortex, 2.0±0.002 g of a water-absorbent resin that was obtained was added into the physiological saline at a time and the time (in seconds) during which after the addition of the water-absorbent resin, the vortex was made to disappear and the liquid surface became flat was measured, with the result that the time was assumed to be the water-absorption rate of physiological saline of the water-absorbent resin.

(5) Median Particle Diameter (Particle Size Distribution)

To 50 g of a water-absorbent resin, 0.25 g of amorphous silica (made by Evonik Degussa Japan, Inc., Carplex #80) was mixed as a lubricant.

JIS standard sieves are combined in the following order from the top: a sieve of 850 μm openings, a sieve of 600 micrometers openings, a sieve of 500 μm openings, a sieve of 400 μm openings, a sieve of 300 μm openings, a sieve of 250 μm openings, a sieve 150 μm openings and a receiving tray.

The water-absorbent resin was introduced into the top of the combined sieves, and then shaken for 20 minutes using a low-tap shaker for classification. After classification, the mass of the water-absorbent resin which remained in each sieve was calculated as a mass percentage relative to the total mass to obtain a particle size distribution. By integrating the amount on each sieve from the one having the largest particle diameter in this particle size distribution, the relationship between the sieve openings and the integrated value of the mass percentage of the water-absorbent resin which remained in the sieves was plotted on logarithmic probability paper. By connecting the plots on the probability paper with a straight line, a particle diameter corresponding to 50 mass % in the integrated mass percentage is taken as the median particle diameter.

The proportion of the water-absorbent resin having a particle diameter from 300 to 400 μm is the proportion of the water-absorbent resin is left on the sieve of 300 μm openings, and likewise, the proportion of the water-absorbent resin having a particle diameter from 150 to 850 μm is a value that is obtained by adding all the proportions of the water-absorbent resin left on the sieves of 150 μm, 250 μm, 300 μm, 400 μm, 500 μm and 600 μm openings.

(6) BET Specific Surface Area

The water-absorbent resin whose particle diameters was adjusted to be passed through a sieve of 400 μm openings and to he held on a sieve of 300 μm openings was used for the measurement of the specific surface area. Then, 10 g of the classified sample was dispersed in 100 g of ethanol, was washed with an ultrasonic cleaning machine (made by SND Co., Ltd., US-103) for 5 minutes and was thereafter filtered with a sieve of 300 μm openings. Then, the same washing operation was performed twice, with the result that a measurement sample subjected to washing three times in total was obtained. This sample was dried under degassing conditions of thermal vacuum exhaust at 100° C. for 16 hours. Thereafter, by a method in which a specific surface area measurement apparatus (made by Quantachrome Co. Ltd., AUTOSORB-1) was used and Krypton gas was used as an adsorption gas, an adsorption isotherm was measured at a temperature of 77 K and the specific surface area was determined from a multipoint BET plot, with the result that the determined specific surface area was assumed to he the BET specific surface area.

4-2. Examples and Comparative Example

Example 1

In Example 1, a 2 L cylindrical round-bottom separable flask with an inner diameter of 110 mm was prepared which was equipped with a reflux condenser, a dropping funnel, a nitrogen gas-introducing tube and stirrer having stirring blades compound of two sets of 4 inclined paddle blades with a blade diameter of 50 mm. To this flask, 300 g of n-heptane was introduced as a hydrocarbon dispersion medium, 0.74 g sucrose stearic acid ester of HLB3 (made by Mitsubishi-Kagaku Foods Corporation, RYOTO sugar ester S-370) was added as a surfactant and 0.74 g of maleic anhydride modified ethylene-propylene copolymer (made by Mitsui Chemicals, Inc., High Wax 1105A) was added as a polymeric dispersion agent, and heated to 80° C. with stirring, and a surfactant was dissolved, and then cooled to 50° C.

Meanwhile, 92 g (1.02 mol) of 80 mass % aqueous acrylic acid was introduced into a 500 mL Erlenmeyer flask, and 102.2 C of 30 mass % aqueous sodium hydroxide was added dropwise while cooling from the outside to perform 75 mol % neutralization. Subsequently, 0.092 g of hydroxyethyl cellulose (made by Sumitomo Seika Chemicals Co., Ltd., HEC AW-15F) as a thickener, 0.092 (0.339 mmol) of 2,2'-azobis(2-amidinopropane)dihydrochloride as an azo based compound, 0.037 g (0.137 mmol) of potassium persulfate as a peroxide, 0.0102 g (0.053 mmol) of ethylene glycol diglycidyl ether as an internal-crosslinking agent and 43.8 g of water were added and dissolved to prepare a first-step aqueous monomer solution.

Then, the number of revolutions of of stirring was set at 550 rpm, and the aqueous monomer solution prepared as described above was added to a separable flask, and the atmosphere in the system was thoroughly replaced with nitrogen. Then, the flask was immersed into a 70° C. water bath to raise temperature, and polymerization was performed for 60 minutes to obtain a first-step polymerized slurry.

Meanwhile, 128.3 g (1.43 mod) of 80 mass % aqueous acrylic acid was introduced to another 500 mL Erlenmeyer flask, and 143.1 g of 30 mass % aqueous sodium hydroxide was added dropwise while cooling from the outside to perform 75 mol % neutralization. Subsequently, 0.129 g (0.475 mmol) of 2,2-azobis(2-amidinopropane)dihydrochloride as an azo based compound, 0.052 g (0.191 mmol) of potassium persulfate as a peroxide, 0.0116 g (0.067 mmol) of ethylene glycol diglycidyl ether as an internal-crosslinking agent and 15.9 g of water were added and dissolved to prepare a second-step aqueous monomer solution.

After the number of revolutions of rotation of the polymerized slurry was changed to 1000 rpm and then cooling the system in the aforementioned separable flask to 25° C., all of the second-step aqueous monomer solution was added to the first-step polymerized slurry, and the atmosphere in the system was thoroughly replaced with nitrogen. Subsequently, the flask was again immersed into a 70° C. water bath to raise temperature, and a second-step polymerization was performed for 30 minutes.

After the second-step polymerization, the reaction liquid was heated to 125° C. in an oil bath, and 241 g of water was removed from the system by refluxing n-heptane in azeotropic distillation of n-heptane and water. Then, 4.42 g (0.507 mmol) of 2 mass % aqueous solution of ethylene glycol diglycidyl ether was added as a post-crosslinking agent, and maintained at 80° C. for 2 hours. Subsequently, drying step was performed by evaporating n-heptane, and then a dried resin was obtained. The dried resin was allowed to pass through a sieve with 1000 μm openings to obtain 233.4 g of a water-absorbent resin in a form of second particles in which spherical primary particles were agglomerated. The water-absorbent resin obtained in this way was evaluated in accordance with the various test methods as described above.

Note that for the water-absorbent resin obtained, the mass proportion of particles from 150 to 850 μm particles relative to the whole proportion was 98.2 mass %, and the mass proportion of particles from 300 to 400 μm particles was 39.4 mass %.

Example 2

In Example 2, the same operation as in Example 1 was performed except that 6.62 g (0.761 mmol) of 2 mass % aqueous solution of ethylene glycol diglycidyl ether added as a post-crosslinking agent was changed, with the result that 232.9 g of a water-absorbent resin in the form of secondary particles in which spherical primary particles were agglomerated was obtained. The water-absorbent resin obtained in this way was evaluated in accordance with the various test methods as described above.

Note that for the water-absorbent resin obtained, the mass proportion of particles from 150 to 850 μm particles relative to the whole proportion was 97.8 mass %, and the mass proportion of particles from 300 to 400 μm particles was 36.5 mass %.

Example 3

In Example 3, the same operation as in Example 1 was performed except that as the internal-crosslinking agent added to the monomer of the first step, the ethylene glycol diglycidyl ether was changed to 0.0202 g (0.116 mmol), that the number of revolutions of stirring was set at 500 rpm and that the polymerization of the first step was performed, with the result that 231.0 g of a water-absorbent resin in the form of secondary particles in which spherical primary particles were agglomerated was obtained. The water-absorbent resin obtained in this way was evaluated in accordance with the various test methods as described above.

Note that for the water-absorbent resin obtained, the mass proportion of particles from 150 to 850 μm particles relative to the whole proportion was 90.7 mass %, and the mass proportion of particles from 300 to 400 μm particles was 24.2 mass %.

Example 4

In Example 4, the same operation as in Example 1 was performed except that as the internal-crosslinking agent added to the monomer of the first step, the ethylene glycol diglycidyl ether was changed to 0.0202 g (0.116 mmol), with the result that 232.1 g of a water-absorbent resin in the form of secondary particles in which spherical primary particles were agglomerated was obtained. The water-absorbent resin obtained in this way was evaluated in accordance with the various test methods as described above.

Note that for the water-absorbent resin obtained, the mass proportion of particles from of 150 to 850 μm particles relative to the whole proportion was 97.9 mass %, and the mass proportion of particles from of 300 to 400 μm particles was 32.6 mass %.

Example 5

In Example 5, the same operation as in Example 1 was performed except that the type of internal-crosslinking agent was changed to polyethylene glycol diglycidyl ether (made by Nagase ChemteX Corporation, EX-861), that the polyethylene glycol diglycidyl ether added to the monomer of the first step was changed to 0.0405 g (0.0369 mmol) and that the polyethylene glycol diglycidyl ether added to the monomer of the second step was changed to 0.0116 g (0.0106 mmol), with the result that 233.8 g of a water-absorbent resin in the form of secondary particles in which spherical primary particles were agglomerated was obtained. The water-absorbent resin obtained in this way was evaluated in accordance with the various test methods as described above.

Note that for the water-absorbent resin obtained, the mass proportion of particles from 150 to 850 μm particles relative to the whole proportion was 95.8 mass %, and the mass proportion of particles from 300 to 400 μm particles was 31.3 mass %.

Example 6

In Example 6, the same operation as in Example 5 was performed except that as the internal-crosslinking agent added to the monomer of the first step, the polyethylene glycol a glycidyl ether (made by Nagase ChemteX Corporation, EX-861) was changed to 0.0810 g (0.0737 mmol), with the result that 232.9 g of a water-absorbent resin in the form of secondary particles in which spherical primary particles were agglomerated was obtained. The water-absorbent resin obtained in this way was evaluated in accordance with the various test methods as described above.

Note that for the water-absorbent resin obtained, the mass proportion of particles from 150 to 850 μm particles relative to the whole proportion was 95.8 mass %, and the mass proportion of particles from 300 to 400 μm particles was 25.5 mass %.

Example 7

In Example 7, the same operation as in Example 5 was performed except that as the internal-crosslinking agent added to the monomer of the first step, the polyethylene glycol diglycidyl ether (made by Nagase ChemteX Corporation, EX-861) was changed to 0.0639 g (0.0581 mmol), that the number of revolutions of the stirring was set at 650 rpm and that the polymerization of the first step was performed, with the result that 231.7 g of a water-absorbent resin in the form of secondary particles in which spherical primary particles were agglomerated was obtained. The water-absorbent resin obtained in this way was evaluated in accordance with the various test methods as described above.

Note that for the water-absorbent resin obtained, the mass proportion of particles from 150 to 850 μm particles relative to the whole proportion was 94.5 mass %, and the mass proportion of particles from 300 to 400 μm particles was 29.8 mass %.

Comparative Example 1

In Comparative Example 1, reverse phase suspension polymerization was performed using only a peroxide, and thus a water-absorbent resin was produced.

Specifically, a 2 L cylindrical round-bottom separable flask with an inner diameter of 110 mm was prepared which was equipped with a reflux condenser, a dropping funnel, nitrogen gas-introducing tube and stirrer having stirring blades compound of two seas of 4 inclined paddle blades with a blade diameter of 50 mm. To this flask, 300 g of n-heptane was introduced as a hydrocarbon dispersion medium, 0.74 g sucrose stearic acid ester of HLB3 (made by Mitsubishi-Kagaku Foods Corporation, Ryoto sugar ester S-370) was added as a surfactant and 0.74 g of maleic anhydride modified ethylene-propylene copolymer (made by Mitsui Chemicals, Inc., High Wax 1105A) were added as a polymeric dispersion agent, and heated to 80° C. with stirring, and a surfactant was dissolved, and then cooled to 50° C.

Meanwhile, 92 g (1.02 mol) of 80 mass % aqueous acrylic acid was introduced into a 500 mL Erlenmeyer flask, and 102.2 g of 30 mass % aqueous sodium hydroxide was added dropwise while cooling from the outside to perform 75 mol % neutralization. Subsequently, 0.092 g of hydroxylethyl cellulose (made by Sumitomo Seika Chemicals Co., Ltd., HEC AW-15F) as a thickener, 0.074 g (0.274 mmol) of potassium persulfate, 0.0184 g (0.106 mmol) of ethylene glycol diglycidyl ether as an internal-crosslinking agent and 43.8 g of ion exchange water were added and dissolved to prepare a first-step aqueous monomer solution.

Then, the number of revolutions of stirring was set at 500 rpm, and the aqueous monomer solution prepared as described above was added to a separable flask, and the atmosphere in the system was thoroughly replaced with nitrogen with stirring. Then, the flask was immersed into a 70° C. water bath to raise increase temperature, and polymerization was performed for 60 minutes to obtain a first-step polymerized slurry.

Meanwhile, 128.8 g (1.43 mol) of 80 mass % aqueous acrylic acid was introduced to another 500 mL Erlenmeyer flask, and 143.1 g of 30 mass % aqueous sodium hydroxide was added dropwise while cooling from the outside to perform 75 mol % neutralization. Then, 0.104 g (0.382 mmol) of potassium persulfate, 0.0129 g (0.074 mmol) of ethylene glycol diglycidyl ether as an internal-crosslinking agent and 15.9 g of ion exchange water were added and dissolved to prepare a second-step aqueous monomer solution.

After the number of revolutions of rotation of the polymerized slurry was changed to 1000 rpm and then cooling the system in the aforementioned separable flask to 25° C., all of the second-step aqueous monomer solution was added to the first-step polymerized slurry, and the atmosphere in the system was thoroughly replaced with nitrogen. Subsequently, the flask was again immersed into a 70° C. water bath to raise temperature, and a second-step polymerization was performed for 30 minutes.

After the second-step polymerization, the reaction liquid was heated to 125° C.; in an oil bath, and 261 g of water was removed from the system by refluxing n-heptane in azeotropic distillation of n-heptane and water. Then, 4.42 g (0.507 mmol) of 2 mass % aqueous solution of ethylene glycol diglycidyl ether was added as a post-crosslinking agent, and maintained at 80° C. for 2 hours. Subsequently, drying step was performed by evaporating n-heptane to obtain a dried resin. The dried resin was allowed to pass through a sieve with 1000 μm openings to obtain 234.5 g of a water-absorbent resin in a form of agglomerated spherical particles. The water-absorbent resin obtained in this way was evaluated in, accordance with the various test methods as described above.

Note that for the water-absorbent resin obtained, the mass proportion of particles from 150 to 850 μm particles relative to the whole proportion was 98.1 mass %, and the mass proportion of particles from 300 to 400 μm particles was 36.9 mass %.

Comparative Example 2

In Comparative Example 2 the same operation as in Comparative Example 1 was performed except that as the internal-crosslinking agent added to the monomer of the first step, the ethylene glycol diglycidyl ether was changed to 0.0156 g (0.090 mmol), that as the internal-crosslinking agent added to the monomer of the second step, the ethylene glycol diglycidyl ether was changed to 0.0155 g (0.089 mmol) and that 6.62 g (0.761 mmol) of 2 mass % aqueous solution of ethylene glycol diglycidyl ether added as a post-crosslinking agent was changed, with the result that 233.6 g of a water-absorbent resin in the form of secondary particles in which spherical primary particles were agglomerated was obtained. The water-absorbent resin obtained in this way was evaluated in accordance with the various test methods as described above.

Note that for the water-absorbent resin obtained, the mass proportion of particles from 150 to 850 μm particles relative to the whole proportion was 93.9 mass %, and the mass proportion of particles from 300 to 400 μm particles was 34.7 mass %.

Comparative Example 3

In Comparative Example 3, as the internal-crosslinking agent added to the monomer of the first step, the ethylene glycol diglycidyl ether was changed to 0.0101 g (0.058 mmol), the number of revolutions of the stirring was set at 500 rpm and the polymerization of the first step was performed. Then, the same operation as in Comparative Example 1 was performed except that as the internal-crosslinking agent added to the monomer of the second step, the ethylene glycol diglycidyl ether was changed to 0.0116 g (0.067 mmol), with the result that 231.8 g of a water-absorbent resin in the form of secondary particles in which spherical primary particles were agglomerated was obtained. The water absorbent resin obtained in this way was evaluated in accordance with the various test methods as described above.

Note that for the water-absorbent resin obtained, the mass proportion of particles from 150 to 850 μm particles relative to the whole proportion was 98.0 mass %, and the mass proportion of particles from 300 to 400 μm particles was 40.7 mass %.

Comparative Example 4

In Comparative Example 4, the same operation as in Example 2 was performed except that as the internal-crosslinking agent added to the monomer of the first step, the ethylene glycol diglycidyl ether was changed to 0.0276 g (0.1584 mmol), that the number of revolutions of the stirring was set at 500 rpm and that the polymerization of the first step was performed, with the result that 232.9 g of a water-absorbent resin in the form of secondary particles in which spherical primary particles were agglomerated was obtained. The water-absorbent resin obtained in this way was evaluated in accordance with the various test methods as described above.

Note that for the water-absorbent resin obtained, the mass proportion of particles from 150 to 850 μm particles relative to the whole proportion was 97.2 mass %, and the mass proportion of particles from 300 to 400 μm particles was 36.4 mass %.

4-3. Evaluation Results

[Evaluation Results of Water-absorbent Resin]

The evaluation results of the water-absorbent resins obtained in examples 1 to 7 and comparative examples 1 to 4 are shown in table 1 below. The polymerization conditions are also shown in table 1.

TABLE 1

| | Polymerization conditions | | | Analysis results | |
|---|---|---|---|---|---|
| | Amount of crosslinking agent (Per mole of monomer) | | | Water-retention | Water-absorption capacity of |
| | Amount of crosslinking agent in first step (mmol) | Amount of crosslinking agent in second step (mmol) | Amount of post-crosslinking agent (mmol) | capacity of physiological saline (g/g) | physiological saline under a load of 4.14 kPa (ml/g) |
| Example1 | 0.057 | 0.047 | 0.207 | 46 | 17 |
| Example2 | 0.057 | 0.047 | 0.310 | 41 | 25 |
| Example3 | 0.114 | 0.047 | 0.207 | 39 | 21 |
| Example4 | 0.114 | 0.047 | 0.310 | 40 | 24 |
| Example5 | 0.036 | 0.007 | 0.207 | 44 | 28 |

TABLE 1-continued

| | | | | | |
|---|---|---|---|---|---|
| Example6 | 0.072 | 0.007 | 0.207 | 41 | 27 |
| Example7 | 0.057 | 0.007 | 0.207 | 42 | 27 |
| Comparative Example1 | 0.104 | 0.052 | 0.207 | 34 | 24 |
| Comparative Example2 | 0.088 | 0.062 | 0.310 | 39 | 19 |
| Comparative Example3 | 0.057 | 0.047 | 0.207 | 41 | 17 |
| Comparative Example4 | 0.155 | 0.047 | 0.310 | 39 | 23 |

| | Analysis results | | | | |
|---|---|---|---|---|---|
| | Particle size distribution | | | | Water-absorption |
| | 150-850 μm Mass proportion (%) | 300-400 μm Mass proportion (%) | Median particle diameter (μm) | 300-400 μm BET specific surface area (m2/g) | rate of physiological saline (Seconds) |
| Example1 | 98.2 | 39.4 | 330 | 0.021 | 64 |
| Example2 | 97.8 | 36.5 | 340 | 0.020 | 77 |
| Example3 | 90.7 | 24.2 | 400 | 0.027 | 50 |
| Example4 | 97.9 | 32.6 | 375 | 0.029 | 43 |
| Example5 | 95.8 | 31.3 | 365 | 0.020 | 66 |
| Example6 | 95.8 | 25.5 | 420 | 0.026 | 51 |
| Example7 | 94.5 | 29.8 | 380 | 0.025 | 53 |
| Comparative Example1 | 98.1 | 36.9 | 370 | 0.033 | 40 |
| Comparative Example2 | 93.9 | 34.7 | 340 | 0.032 | 35 |
| Comparative Example3 | 98.0 | 40.7 | 360 | 0.039 | 37 |
| Comparative Example4 | 97.2 | 36.4 | 370 | 0.032 | 40 |

As found from table 1, in the method of manufacturing the water-absorbent resin according to Examples 1 to 7, the water-absorbent resin whose BET specific surface area was controlled was obtained.

[Evaluation Test Results of Absorbent Material and Absorbent Article Using Water Absorbent Resin]

Then, absorbent material and absorbent articles were produced using the water-absorbent resins obtained in Examples 1, 2, 4 and 6 and Comparative Examples 1, 3 and 4 in methods described below and were evaluated.

(1) Production of Absorbent Material and Absorbent Article

Example 8

12 g of the water-absorbent resin obtained in Example and 12 g of crushed pulp (made by Rayonier, Inc. Rayfloc) were used, and were uniformly mixed by air papermaking, with the result that a sheet-shaped absorbent material core having a size of 40 cm×12 cm was produced. Then, while the upper and lower parts of the absorbent core were being sandwiched between two sheets of tissue paper equal in size to the absorbent material core and having a basis weight of 16 g/m², a load of 196 kPa was pressed over for 30 seconds, with the result that an absorbent material was produced. Furthermore, on the upper surface of the absorbent material, a polyethylene-polypropylene air-through type porous liquid permeable sheet equal in size to the absorbent material core and having a basis weight of 22 g/m² was arranged, and a polyethylene liquid-impermeable sheet having the same size and the same basis weight of liquid permeable sheet was arranged on the lower surface, and thus the absorbent material was sandwiched, with the result that an absorbent article in which the basis weight of the water-absorbent resin was 250 g/m² and the basis weight of the hydrophilic fiber was 250 g/m² was formed.

Examples 9 to 11 and Comparative Examples 5 to 7

In Examples 9 to 11 and Comparative Examples 5 to 7, the same operation as in Example 8 was performed except that instead of the water-absorbent resin obtained in Example 1, the water-absorbent resins obtained in Examples 2, 4 and 6 and Comparative Examples 1, 3 and 4 were used, with the result that absorbent articles were obtained. The obtained absorbent articles were respectively assumed to be the absorbent articles in Examples 9, 10 and 11 and Comparative Examples 5, 6 and 7.

(2) Preparation of Test Liquid

As a test liquid, NaCl, $CaCl_2$ and $MgSO_4$ were mixed in ion-exchange water such that NaCl was 0.780 mass %, $CaCl_2$ was 0.022 mass % and $MgSO_4$ was 0.038 mass %, and were dissolved and furthermore, a small amount of Blue No. 1 was mixed. In this way, the test liquid was prepared.

(3) Permeation Time

The absorbent article was first placed on a horizontal stage. On the center portion of the absorbent article, a measurement apparatus incorporating a liquid pouring cylinder having an inside diameter of 3 cm was placed, and 80 mL of the test liquid was poured into the cylinder at a time and a stopwatch was used to measure the time until the test liquid was made to disappear completely, with the result that the time was assumed to be the first permeation time (in seconds), Then, the cylinder described above was removed, the absorbent article was stored in the present state and both when 30 minutes had elapsed and when 60 minutes had elapsed since the start of the first round of the pouring of the test liquid, the measurement apparatus was used in the position as in the first round, and the same operation was performed, with the result that the second and third permeation times (in seconds) were measured.

The total time of the first to third rounds was assumed to be the total permeation time. It is said that as the permeation time is shorter, the absorbent article was more preferable.

(4) Re-wet Amount 120 minutes after the state of the first round of the pouring of the test liquid in the measurement of the permeation time described above, in, the vicinity of the position on the absorbent article where the test liquid was poured, filter paper 10 cm square whose mass (Wd (g), about 50 g) was previously measured was put, and thereon, a weight having a bottom surface of 10 cm×10 cm and a mass of 5 kg was placed. The load was placed for 5 minutes, and the mass (We (g)) of the filter paper was measured, with the result that the increased mass was assumed to be the re-wet amount (g). It is said that as the re-wet amount was decreased, the absorbent article was more preferable.

re-wet amount (g)=$We-Wd$ (5) Diffusion Length

Within 5 minutes after the measurement of the re-wet amount described above, the dimension (cm) of spread of the absorbent article in the longitudinal, direction into which the test liquid is penetrated was measured. Values after the decimal, point were rounded off.

[Evaluation Results of Absorbent Article]

Then, in table 2 below, the evaluation results of the absorbent articles obtained in. Examples 8 to 11 and Comparative Examples 5 to 7 are shown.

TABLE 2

| | 300-400 μm BET specific surface area | Water-absorption rate of physiological saline | Permeation time(Seconds) | | | | Re-wet amount | Diffusion length |
|---|---|---|---|---|---|---|---|---|
| | (m²/g) | (Seconds) | 1 | 2 | 3 | Total | (g) | (cm) |
| Example8 | 0.021 | 64 | 24 | 28 | 34 | 86 | 2.9 | 24 |
| Example9 | 0.020 | 77 | 24 | 28 | 35 | 87 | 4.5 | 25 |
| Example10 | 0.029 | 43 | 24 | 28 | 33 | 85 | 15.9 | 23 |
| Example11 | 0.026 | 51 | 24 | 27 | 32 | 83 | 9.7 | 24 |
| Comparative Example5 | 0.033 | 40 | 23 | 28 | 33 | 84 | 28.6 | 23 |
| Comparative Example6 | 0.039 | 37 | 24 | 33 | 53 | 110 | 29.8 | 21 |
| Comparative Example7 | 0.032 | 40 | 24 | 33 | 37 | 94 | 23.8 | 22 |

As shown in table 2, compared with Comparative Examples, in the absorbent articles using the water-absorbent resins having the BET specific surface area and the water-absorption rate appropriate in Examples, the performances of the permeation time and the re-wet amount were excellent.

EXPLANATION OF REFERENCE. NUMERALS

X measurement apparatus
1 buret part
2 conduit
3 measurement stage
4 measurement part
5 water-absorbent resin

The invention claimed is:

1. A water-absorbent resin that is obtained by polymerizing a water-soluble ethylenically unsaturated monomer in presence of an internal-crosslinking agent, wherein
   a monomer of 70 to 100 mol % in the water-soluble ethylenically unsaturated monomer is acrylic acid or salt thereof,
   a water-absorption rate of physiological saline in the water-absorbent resin is 40 to 80 seconds,
   a mass proportion of particles from 150 to 850 μm in diameter in the entire water-absorbent resin is 85 mass % or more, and a mass proportion of particles from 300 to 400 μm in diameter is 20 mass % or more and
   a BET specific surface area of particles classified into 300 to 400 μm is less than 0.03 m²/g.

2. The water-absorbent resin according to claim 1, wherein a median particle diameter of the water-absorbent resin is 200 to 600 μm.

3. A water-absorbing agent that is obtained by mixing the water-absorbent resin according to claim 1 with an inorganic fine powder.

4. An absorbent article that is formed by using an absorbent material containing the water-absorbent resin according to claim 1.

5. An absorbent article that is formed by using an absorbent material containing the water-absorbing agent according to claim 3.

6. The water-absorbent resin according to claim 1, wherein a water-absorption rate of physiological saline in the water-absorbent resin is 43 to 80 seconds.

7. The water-absorbent resin according to claim 1, wherein the water-absorbent resin is obtained by polymerizing a water-soluble ethylenically unsaturated monomer in presence of an azo compound, a peroxide and an internal-crosslinking agent.

8. A method of manufacturing the water-absorbent resin of claim 7, wherein when reverse phase suspension polymerization of two steps or more is performed on a water-soluble ethylenically unsaturated monomer in a hydrocarbon dispersion medium in presence of at least an azo compound, a peroxide and an internal-crosslinking agent,
   the polymerization at each step being performed in the presence of an azo compound and a peroxide,
   a used amount of the internal-cros slinking agent at the time of the polymerization of a first step for 1 mole of the water-soluble ethylenically unsaturated monomer used at the time of the polymerization of the first step is adjusted to fall within a range of 0.015 to 0.150 mmol and the polymerization is performed such that a BET specific surface area of secondary particles formed by agglomeration of primary particles obtained is controlled.

9. The method of manufacturing a water-absorbent resin according to claim 8, wherein a used amount (mole) of the internal-crosslinking agent at the time of the polymerization of the second and later steps for 1 mole of the water-soluble ethylenically unsaturated monomer of the second and later steps, is 90% or less of a used amount (mole) of the internal-crosslinking agent used at the time of the polymerization of the first step for 1 mole of the water-soluble ethylenically unsaturated monomer used at the time of the polymerization of the first step.

10. The method of manufacturing a water-absorbent resin according to claim 8, wherein the BET specific surface area of the secondary particles that are formed by agglomeration of the primary particles and that are classified into 300 to 400 μm is controlled to be less than 0.03 $m^2/g$.

* * * * *